United States Patent [19]
Crawford, II

[11] Patent Number: 5,467,482
[45] Date of Patent: Nov. 21, 1995

[54] SELF SUPPORTING SIDELESS AND WAISTLESS TANNING BRIEF

[76] Inventor: William E. Crawford, II, 6112 Edgemoor, Houston, Tex. 77081

[21] Appl. No.: 304,783

[22] Filed: Sep. 12, 1994

[51] Int. Cl.⁶ .................. A41D 7/00; A41B 9/00
[52] U.S. Cl. .................. 2/67; 2/400; 2/402; 2/406; 2/73
[58] Field of Search .................. 2/400, 401, 402, 2/403, 404, 405, 406, 407, 408, 67, 73; 450/81; 11/80

[56] References Cited

U.S. PATENT DOCUMENTS

| | | | |
|---|---|---|---|
| 2,534,934 | 12/1950 | Viniegra | 2/67 |
| 3,339,208 | 9/1967 | Marbach | 2/67 |
| 4,937,886 | 7/1990 | Ellis | 2/323 |
| 4,982,450 | 1/1991 | D'Huissier | 2/402 |
| 5,114,419 | 5/1992 | Daniel et al. | 2/402 |
| 5,313,669 | 5/1994 | Rasdell et al. | 2/112 X |
| 5,347,657 | 9/1994 | Unsell | 2/401 |

*Primary Examiner*—Jeanette E. Chapman
*Attorney, Agent, or Firm*—Kenneth A. Roddy

[57] ABSTRACT

A self supporting thong type brief has no side or waist portions and can be shaped to custom fit the wearer for substantial exposure of the midsection and buttocks area and is particularly suited for sun bathing and tanning. In a preferred embodiment the tanning brief has an interior frame formed of a length of small diameter resilient malleable wire bent to form a relatively short front portion, opposed elongate side portions which extend rearwardly and angularly inward from said front portion and converge toward each other and then extend rearwardly parallel to one another to form a longitudinal rear portion. At least the longitudinal rear portion of the frame is covered by a soft cushioning material. The frame and cushioning material is completely enclosed by a fabric covering. The brief is preferably packaged and sold in a straight configuration, and is thereafter manually shaped into a generally C-shaped configuration curved along its length to custom fit the body of an individual wearer. When worn, the brief covers the genital area, extends rearwardly along the crotch area, and curves upwardly between the buttocks of the wearer, and is resiliently maintained on the body of the wearer by the spring tension of the frame.

8 Claims, 2 Drawing Sheets

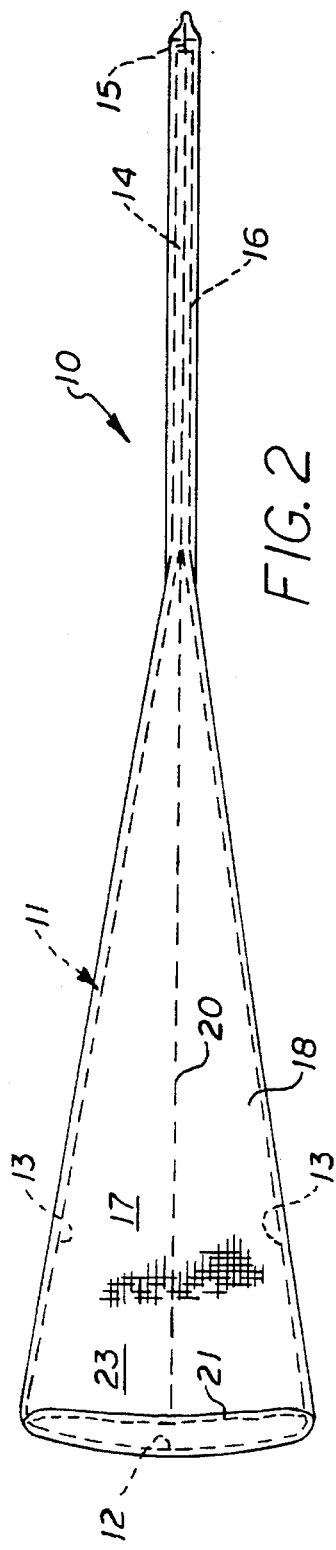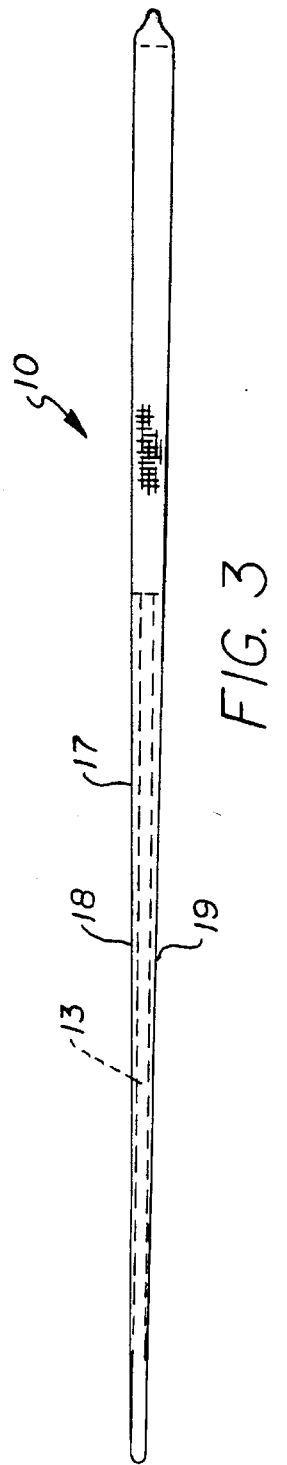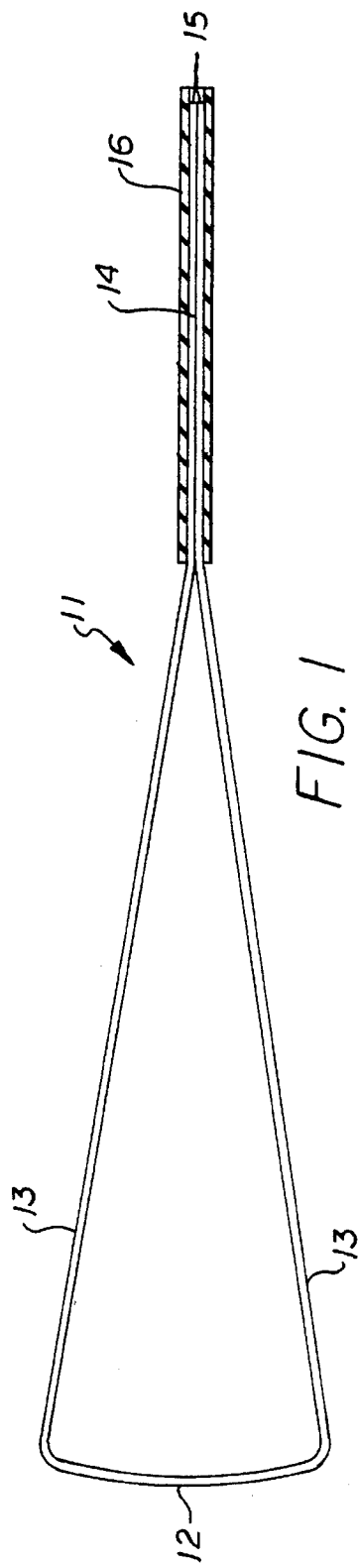

5,467,482

SELF SUPPORTING SIDELESS AND WAISTLESS TANNING BRIEF

BACKGROUND OF THE INVENTION

1. Field of the Invention

This invention relates generally to thong type bikini bottoms and briefs, and more particularly to a self supporting thong type brief which has no side or waist portions and can be shaped custom to fit the wearer for substantial exposure of the midsection and buttocks area and is particularly suited for sun bathing and tanning.

2. Brief Description of the Prior Art

Thong-type bikini swimsuit bottoms and briefs are known in the art. However, most of these prior art garments have a fabric front section that covers the frontal area of the wearer, a midsection that extends along the crotch, and a rear portion that extends upwardly between the buttocks, and the front and rear portions are secured to a waist band or string which encircles the waist of the wearer.

These prior art types of garments will leave a white outline of the shape of the garment when the wearer is exposed to the sun or the lamps of a tanning booth. This white outline will often be seen when the person wears a swimsuit or other piece of clothing having a shape different from the one used to obtain the tan.

The present invention overcomes these problems and is distinguished over the prior art in general, and these patents in particular by a self-supporting thong type brief which has no side or waist portions and can be shaped to custom fit the wearer for substantial exposure of the midsection and buttocks area and is particularly suited for sun bathing and tanning. In a preferred embodiment the tanning brief has an interior frame formed of a length of small diameter resilient malleable wire bent to form a relatively short front portion, opposed elongate side portions which extend rearwardly and angularly inward from said front portion and converge toward each other and then extend rearwardly parallel to one another to form a longitudinal rear portion. At least the longitudinal rear portion of the frame is covered by a soft cushioning material. The frame and cushioning material is completely enclosed by a fabric covering. The brief is preferably packaged and sold in a straight configuration, and is thereafter manually shaped into a generally C-shaped configuration curved along its length to custom fit the body of an individual wearer. When worn, the brief covers the genital area, extends rearwardly along the crotch area, and curves upwardly between the buttocks of the wearer, and is resiliently maintained on the body of the wearer by the spring tension of the frame.

SUMMARY OF THE INVENTION

It is therefore an object of the present invention to provide a thong-type brief which has no side or waist portions for substantial exposure of the midsection and buttocks area of the wearer when sun bathing or tanning.

It is another object; of this invention to provide a thong-type brief which has no side or waist portions and can be shaped to custom fit the wearer.

Another object of this invention is to provide a thong-type brief which is self supported on the wearer and does not require a waist encircling band or supporting member.

Another object of this invention is to provide a thong-type brief which will not leave a white outline around the waist or the sides of the legs of a wearer after sunbathing or tanning.

A further object of this invention is to provide an attractive thong-type brief which may be worn by dancers, models, entertainers, and contestants in beauty pageants, swim suit and body building competitions.

A still further object of this invention is to provide a thong-type brief which is simple in construction, economical to manufacture, and attractive in appearance.

Other objects of the invention will become apparent from time to time throughout the specification and claims as hereinafter related.

The above noted objects and other objects of the invention are accomplished by a self-supporting thong type brief which has no side or waist portions and can be shaped to custom fit the wearer for substantial exposure of the midsection and buttocks area and is particularly suited for sun bathing and tanning. In a preferred embodiment the tanning brief has an interior frame formed of a length of small diameter resilient malleable wire bent to form a relatively short front portion, opposed elongate side portions which extend rearwardly and angularly inward from said front portion and converge toward each other and then extend rearwardly parallel to one another to form a longitudinal rear portion. At least the longitudinal rear portion of the frame is covered by a soft cushioning material. The frame and cushioning material is completely enclosed by a fabric covering. The brief is preferably packaged and sold in a straight configuration, and is thereafter manually shaped into a generally C-shaped configuration curved along its length to custom fit the body of an individual wearer. When worn, the brief covers the genital area, extends rearwardly along the crotch area, and curves upwardly between the buttocks of the wearer, and is resiliently maintained on the body of the wearer by the spring tension of the frame.

BRIEF DESCRIPTION OF THE DRAWINGS

FIG. 1 is a top plan view of the interior frame of the sideless and waistless tanning brief in accordance with the present invention shown without a cover.

FIG. 2 is a top plan view of the sideless and waistless tanning brief with the cover on the frame shown in a straight condition prior to shaping it to fit the wearer.

FIG. 3 is a side elevation of the sideless and waistless tanning brief in the straight condition prior to shaping it to fit the wearer.

DESCRIPTION OF THE PREFERRED EMBODIMENT

Figure 4:
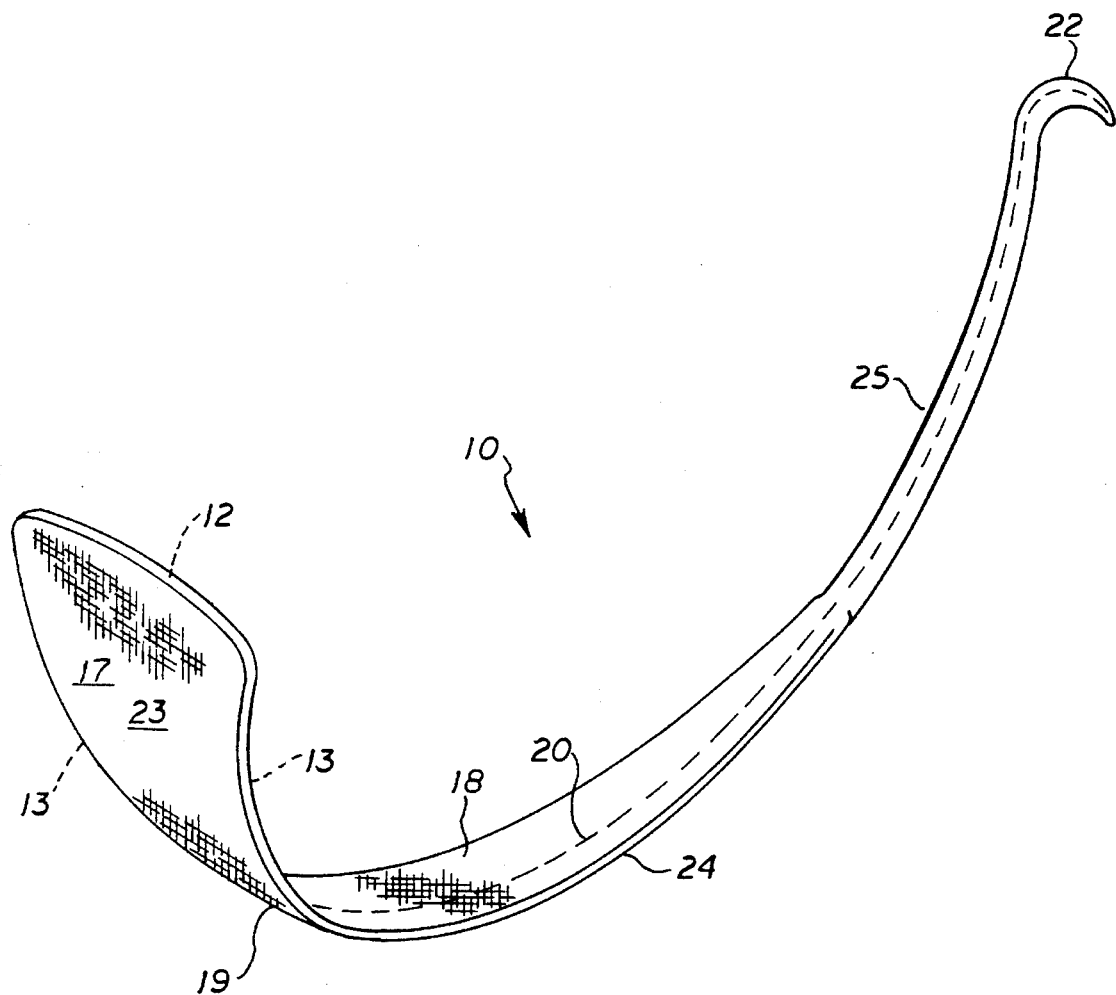
FIG. 4 is a perspective view of the sideless and waistless tanning brief in accordance with the present invention after being shaped to fit the wearer.

Referring to the drawings by numerals of reference, there is shown in FIGS. 1–3, a preferred sideless and waistless tanning brief 10 in a straight condition prior to shaping it to fit the wearer. FIG. 4 shows the brief after it has been shaped to fit the wearer, as described hereinafter.

As best seen in FIG. 1, the sideless and waistless tanning brief 10 has an interior bent wire frame 11 which is initially has an elongate generally triangular shape. The wire frame 11 is constructed of a length of wire which is bent to form a relatively short front portion 12, opposed elongate side portions 13 which curve to extend rearwardly and angularly inward from the front portion and converge toward each other and then extend rearwardly parallel to one another to form a longitudinal straight rear portion 14. The wire portions 12–14 are in the same plane to form a straight configuration in the longitudinal plane. The preferred wire material is small diameter spring wire, such as stainless steel, which is sufficiently resilient and malleable to be formed and will resiliently retain its shape after being formed.

The straight portion 14 of the parallel wire sections including the terminal ends 15 of the wires is covered by a length of soft elastomeric tubing 16, such as surgical tubing which extends a short distance beyond the terminal ends 15. The tubing 16 maintains parallel wires forming the straight rear portion 14 together. The tubing 16 also forms a soft cushion and protects the terminal ends 15 of the wire from contacting the wearer and penetrating the fabric cover (described below).

As shown in FIGS. 2–4, the bent wire frame 11 including the tubing 16 is completely enclosed by a fabric covering 17 which extends over the top and bottom of the frame along its length to form a top layer 18 and bottom layer 19.

The covering 17 may be constructed and installed on the frame by various methods. For example, the fabric material may be cut to a generally triangular shape larger than the periphery of the frame with the longitudinal side edges and narrow end secured together by stitching 20 or other conventional means leaving the wide end open to form a generally funnel-shaped tubular sheath. The wire frame 11 with the tubing 16 installed thereon is then inserted into the sheath from its open wide end and the stitching is positioned to lie along the longitudinal center of the frame on one side. The open end of sheath is then folded over the short front portion 12 of the wire frame 11 and secured to the layer 18 of fabric material by stitching 21 or other conventional means, such that any stitching or seams will be on the same side of the frame.

In a preferred embodiment, the sideless and waistless tanning brief 10 is packaged and sold in a straight condition as shown in FIGS. 2 and 3. Any convenient cylindrical object, such as a can or rolling pin, can be used to shape the tanning brief to fit the body of the wearer. The front portion 12 of the brief is placed on the cylindrical object, and is manually rolled over the cylindrical surface until the brief assumes a generally "C" shaped curved configuration as shown in FIG. 4. The larger the cylindrical object, the larger the garment size. When properly shaped, the size of the curve of the brief will be slightly smaller than the corresponding parts of the body on which it fits. A small portion at the extreme rear of the curved brief may also be recurved outwardly 22 from the "C" shape to position the terminal ends of the wire frame away from the body of the wearer.

As seen in FIG. 4, when worn, the wider front triangular portion 23 of the brief 10 covers the genital area, the curved middle portion 24 extends rearwardly along the crotch area, and the cushioned rear portion 25 curves upwardly between the buttocks of the wearer. The brief 10 is maintained on the body of the wearer by the spring tension of the wire frame 11.

While this invention has been described fully and completely with special emphasis upon a preferred embodiment, it should be understood that within the scope of the appended claims the invention may be practiced otherwise than as specifically described herein.

I claim:

1. A sideless and waistless thong-type tanning brief comprising in combination;

an elongate generally triangular shaped frame of small diameter resilient malleable wire bent to form a relatively short front portion, opposed elongate side portions which extend rearwardly and angularly inward from said front portion and converge toward each other and then extend rearwardly parallel together to form a longitudinal rear portion, a length of soft elastomeric tubing encircling said parallel rearwardly extending portions of said wire to hold said parallel rearwardly extending portions together and form a cushioned longitudinal rear portion, and a fabric covering completely enclosing said frame and said soft elastomeric tubing, said enclosed frame being formed into a generally C-shaped configuration curved along its length and resiliently maintained in said C-shaped configuration, such that when worn, said brief will cover the genital area, extend rearwardly along the crotch area, and curve upwardly between the buttocks of the wearer with said cushioned longitudinal rear portion disposed along the crotch area and between the buttocks, and will be maintained on the body of the wearer by the spring tension of said frame in said C-shaped configuration.

2. The tanning brief according to claim 1 in which said length of soft elastomeric tubing is surgical tubing.

3. The tanning brief according to claim 1 in which said enclosed frame is formed into a generally C-shaped configuration curved along its length and the terminal end of said cushioned longitudinal rear portion is recurved outwardly from the C-shaped configuration to position the rearmost end of said frame away from the body of the wearer.

4. An improved sideless and waistless thong-type tanning brief of the type having an elongate generally triangular shaped frame of bent wire covered by a fabric and having a front portion which covers the genital area and a rearwardly extending portion which is received along the crotch area and curves upwardly between the buttocks of the wearer, the improvement comprising;

an elongate generally triangular shaped frame of small diameter resilient malleable wire bent to form a relatively short front portion and opposed elongate side portions which extend rearwardly and angularly inward from said front portion and converge toward each other and then extend rearwardly parallel together to form a longitudinal rear portion, and a length of soft elastomeric tubing encircling said parallel rearwardly extending portions of said wire to hold said parallel rearwardly extending portions together and form a cushioned longitudinal rear portion, said frame and said soft elastomeric tubing being completely enclosed in the fabric covering.

5. The improved tanning brief according to claim 4 wherein said enclosed frame is formed into a generally C-shaped configuration curved along its length and the terminal end of said cushioned longitudinal rear portion is recurved outwardly from the C-shaped configuration to position the rearmost end of said frame away from the body of the wearer.

6. A method of making a sideless and waistless thong-type tanning brief comprising the steps of:

bending a length of small diameter resilient malleable wire to form an elongate generally triangular shaped frame having a relatively short front portion, opposed elongate side portions which extend rearwardly and angularly inward from said front portion and converge toward each other and then extend rearwardly parallel together to form a longitudinal rear portion;

installing a length of soft elastomeric tubing on said parallel rearwardly extending portions of said wire to hold said parallel rearwardly extending portions together and form a cushioned longitudinal rear portion;

forming a triangular generally funnel-shaped sheath of fabric material having a wide end, longitudinal sides, and a narrow end corresponding to the periphery of said frame, said longitudinal sides and narrow end secured together and said wide end being open;

installing said frame into said sheath from said open wide end; and thereafter closing said open wide end and securing it in the closed condition such that said frame and said soft elastomeric tubing are completely enclosed in said fabric sheath.

7. The method according to claim 6 including the further step of shaping said enclosed frame and said soft elastomeric tubing into a generally C-shaped configuration curved along its length such that, when worn, said brief will cover the genital area, extend rearwardly along the crotch area, and curve upwardly between the buttocks of the wearer with said cushioned longitudinal rear portion disposed along the crotch area and between the buttocks, and will be maintained on the body of the wearer by the spring tension of said frame in said C-shaped configuration.

8. The method according to claim 7 including the further step of recuring the terminal end of said cushioned longitudinal rear portion outwardly from the C-shaped configuration to position the rearmost end of said frame away from the body of the wearer.

\* \* \* \* \*